US011633408B2

(12) United States Patent
Zugmaier et al.

(10) Patent No.: US 11,633,408 B2
(45) Date of Patent: *Apr. 25, 2023

(54) PREVENTION OF ADVERSE EFFECTS CAUSED BY CD3 SPECIFIC BINDING DOMAINS

(71) Applicant: AMGEN RESEARCH (MUNICH) GMBH, Munich (DE)

(72) Inventors: Gerhard Zugmaier, Munich (DE); Dirk Nagorsen, Munich (DE); Juergen Scheele, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/157,985

(22) Filed: Oct. 11, 2018

(65) Prior Publication Data

US 2019/0142846 A1    May 16, 2019

Related U.S. Application Data

(63) Continuation of application No. 13/884,497, filed as application No. PCT/EP2011/068862 on Oct. 27, 2011, now Pat. No. 10,130,638.

(60) Provisional application No. 61/412,229, filed on Nov. 10, 2010.

(51) Int. Cl.
*A61K 31/573* (2006.01)
*A61K 39/395* (2006.01)
*C07K 16/28* (2006.01)
*A61K 39/00* (2006.01)

(52) U.S. Cl.
CPC ........ *A61K 31/573* (2013.01); *A61K 39/3955* (2013.01); *A61K 39/39558* (2013.01); *C07K 16/2803* (2013.01); *C07K 16/2809* (2013.01); *A61K 2039/505* (2013.01); *A61K 2300/00* (2013.01); *C07K 2317/31* (2013.01)

(58) Field of Classification Search
CPC .............. A61K 31/573; A61K 39/3955; A61K 39/39558; A61K 2039/505
See application file for complete search history.

(56) References Cited

U.S. PATENT DOCUMENTS

2009/0191201 A1   7/2009   Heiss et al.

FOREIGN PATENT DOCUMENTS

| CA | 2606081 A1 | 11/2006 |
| CN | 101331151 A | 12/2008 |
| JP | 2002-512020 A | 4/2002 |
| JP | 2009-519257 A | 5/2009 |
| WO | WO-1999/54440 A1 | 10/1999 |
| WO | WO-2007/068354 A1 | 6/2007 |
| WO | WO-2011/051307 A1 | 5/2011 |

OTHER PUBLICATIONS

B-cell chronic lymphocytic leukemia, Wikipedia, the free encyclopedia, http://en.wikipedia.org/B-cell_chronic_lymphocytic_leukiemia (Mar. 3, 2015).
Baeuerle, et al., "BITE: a New Class of Antibodies That Recruit T-Cells," Drugs of the Future. 33(2):137-147 (2008).
Bargou "1Blinatumomab (CD3/CD19 BiTE antibody) results in a high response rate in pateitns with relapsed non-hodgkin lymphoma (NHL) including MCL and DLBCL," (2011), 11th Internal Conf on Malignant Lymphoma, Switz.
Brandi et al., The effect of dexamethasone on polyclonal T cell activation and redirected target el lysis as induced by a CD19/CD3-bispecific single-chain antibody construct, Can. Immunol. Immunother. 56(10):1551-63 (2007).
Christian Brandl et al. "The effect of dexamethasone on polyclonal T cell activation and redirected target cell lysis as induced by a CD19/CD3-bispecific single-chain antibody construct," Cancer Immunology, Immunotherapy. 46(10):1551-1563 (2007).
Goebler, et al., "CD3/CD19 Bispecific Bite (R) Antibody Blinatumomab Treatment of Non-Hodgkin Lymphoma (NHL) Patients: 60 mu G/M-2/D by Continuous Infusion is Tolerable and Results in Durable Responses," Haematologica—The Hematology Journal. 94(2):230 (2010).
Hoffman et al., "Serial Killing of Tumor Cells by Cytotoxic T Cells Redirected with a CD19-/CD3-Bispecific single-chain antibody construct," International Journal of Cancer. 115(1):98-104 (2005).
International Search Report and Written Opinion from PCT/EP2011/068862 dated May 18, 2012.
Nagorsen Dirk et al., Confirmation of Safety, Efficacy and response Duration in Non-Hodgkin Lymphoma Patients Treated with 60 mu g/m(2)/d of BiTE (R) Antibody Blinatumomab Database Accession No. PREV20100353716 abstract., Blood 114: 1066 (2010).
Nagorsen et al., Immunotherapy of lymphoma and leukemia with T-cell engaging BiTE antibody Blinatumomab, Leukemia & Lymphoma. 50(6):886 (2009).
Sebastian et al., Treatment of non-small cell lunch cancer patients with the trifunctional monoclonal antibody catumaxomab (anti-EpCAM x anti-CD3): A phase I study. Cancer Immunol. Immunother. 56(10): 1637-44 (2007).
Viardot et al., Treatment of patients with non-Hodgkin lymphoma (NHL) with CD19/CD3 bispectific antibody blinatumomab (MT103): Double-step dose increase to continuous infusion of 60 g/m²/d is tolerable and highly effective, ASH Annual Meeting Abs. 116:2880 (2010).
Wolf et al., "BITEs: Bispecific Antibody Constructs with Unique Anti-Tumor Activity," Drug Discov. Today. 10(18):1237-1244 (2005).

(Continued)

Primary Examiner — Olga N Chernyshev
(74) Attorney, Agent, or Firm — Marshall, Gerstein & Borun LLP

(57) ABSTRACT

The present invention relates to a glucocorticoid (GC) for use in the amelioration, treatment or prophylaxis of neurological/psychiatric adverse events caused by a CD3 binding domain. Kits comprising a GC, a CD3 binding domain and instructions for use which indicate that the GC is to be employed for the treatment amelioration and/or prophylaxis of neurological adverse events caused by said CD3 binding domain, are also disclosed.

16 Claims, No Drawings
Specification includes a Sequence Listing.

(56) References Cited

OTHER PUBLICATIONS

Guarino et al., "EFNS guidelines on management of neurological problems in liver transplantation," *European Journal of Neurology* 13: 2-9 (2006).
Encephalopathy, Wikipedia, the free encyclopedia, http://en.wikipedia.org/wiki/Encephalopathy (Feb. 9, 2019).
Muromonab-CD3, Wikipedia, the free encyclopedia, http://en.wikipedia.org/wiki/Muromonab-CD3 (Jan. 23, 2018).
Inaba et al., Glococorticoid use in acute lymphoblastic leukemia: comparison of prednisone and dexamethasone, *Lancet Oncol.* 11(11): 1096-1106 (2010).

PREVENTION OF ADVERSE EFFECTS CAUSED BY CD3 SPECIFIC BINDING DOMAINS

The present invention relates to a glucocorticoid (GC) for use in the amelioration, treatment or prophylaxis of neurological/psychiatric adverse events caused by a CD3 binding domain. Kits comprising a GC, a CD3 binding domain and instructions for use which indicate that the GC is to be employed for the treatment amelioration and/or prophylaxis of neurological adverse events caused by said CD3 binding domain, are also disclosed.

Antibody-based cancer therapies require a target antigen firmly bound to the surface of cancer cells in order to be active. By binding to the surface target, the antibody can directly deliver a deadly signal to the cancer cell or indirectly by, for example, recruiting a cytotoxic T cell, if it is a bispecific antibody. In an ideal treatment scenario, a target antigen is abundantly present and accessible on every cancer cell and is absent, shielded or much less abundant on normal cells. This situation provides the basis for a therapeutic window in which a defined amount of the antibody-based therapeutic effectively hits cancer cells but spares normal cells.

Though binding domains like antibodies are an effective means in treating many disorders, in particular cancer, their administration is not necessarily devoid of side effects. Adverse effects may cause a reversible or irreversible change in the health status of a patient. As adverse effects could be harmful and undesired, it is highly desirable to avoid them. However, though it is known that a medicament can cause adverse effects, its prescription and administration could not be avoided or is accepted, since the medicament has an outstanding beneficial therapeutic effect or may even be life-saving.

In clinical trials, a general distinction can be made between adverse effects (AEs) and serious adverse effects (SAEs). Specifically, adverse effects can be classified in 5 grades in accordance with the Common Terminology Criteria for Adverse Events (CTCAE). Grade 1 relates to mild AE, Grade 2 to moderate AE, Grade 3 to severe AE, Grade 4 to life-threatening or disabling AE, while Grade 5 means death related to AE.

An adverse effect observed in antibody therapy is the occurrence of infusion-related side effects, such as the cytokine release syndrome ("CRS"). Other adverse side effects described to be associated with CRS are fatigue, vomiting, tachycardia, hypertension, back pain, but also central nervous system reactions (CNS reactions, neurological and/or psychiatric), such as seizures, encephalopathy, cerebral edema, aseptic meningitis, and headache.

Adverse events such as cytokine release and neurological/psychiatric reactions have not only been observed with antibodies binding to the T cell receptor but also with a CD19×CD3 bispecific single chain antibody binding to the CD3 part of the T cell receptor (called Blinatumomab (MT103)). Blinatumomab (MT103) is a lymphoma-directed, recombinant bispecific single-chain CD19×CD3 antibody that binds to CD19 on the surface of almost all B cells and B tumor cells and concomitantly can engage a T cell, thereby triggering the T-cell to kill the target B cell or B tumor cell. Blinatumomab consists of four immunoglobulin variable domains assembled into a single polypeptide chain. Two of the variable domains form the binding site for CD19, a cell surface antigen expressed on most B cells and B tumor cells. The other two variable domains form the binding site for the CD3 complex on T cells. Blinatumomab is designed to direct the body's cytotoxic, or cell-destroying, T cells against tumor cells, and represent a new therapeutic approach to cancer therapy. Blinatumomab is presently in clinical trials.

As described, for instance, in WO 99/54440, adverse effects have been observed in a previous study performed with Blinatumomab applied in repeated bolus infusions to a patient with B-cell derived chronic lymphatic leukaemia (B-CLL). As shown in FIGS. 19 and 20 of WO 99/54440, release of TNF, IL-6 and IL-8 has been found in response to each of the administered 20 minute-infusions of 3 microgram and 10 microgram of the mentioned bispecific single chain antibody, respectively, with cytokine release after each administration. Maximal cytokine release was observed after administration of 10 microgram of bispecific single chain antibody. In a following clinical trial study, in which escalating doses of the CD19×CD3 bispecific single chain antibody have been administered to patients with B cell malignancies as bolus infusions, adverse effects have also been observed. According to a retrospective analysis, 7 out of 22 patients showed an early neurological reaction, including, for example, confusion, ataxia, speech disorder, or disorientation.

As shown in Bargou et al. (Science 321 (2008): 974-7), doses as low as 0.005 milligrams per square meter per day continuously administered to non-Hodgkin's lymphoma patients over four weeks led to an elimination of lymphoma target cells in blood. Partial and complete tumor regressions were first observed at a dose level of 0.015 milligrams/m$^2$/d, and all seven patients treated at a dose level of 0.06 milligrams/m$^2$/d experienced a tumor regression (Bargou et al., cited above). The CD19×CD3 bispecific single chain antibody also led to clearance of tumor cells from bone marrow and liver. However, though this (still ongoing) study established clinical proof of concept for the therapeutic potency of the CD19×CD3 bispecific single chain antibody format in the treatment of blood-cell derived cancer, neurological reactions have been found in the course of the aforementioned clinical trial. In order to get these undesired side effects under control, the mode of administration of the CD19×CD3 bispecific single chain antibody has been changed in that it has been switched over from bolus infusion to a continuous intravenous administration of said antibody for a longer period of time. Accordingly, since Blinatumomab is a very promising candidate medicament for treating non-Hodgkin's lymphoma (NHL), such as, diffuse large B-cell lymphoma (DLBCL), follicular lymphoma and mantle cell lymphoma (MCL), acute lymphoblastic leukemia (ALL), and/or chronic lymphocytic leukemia (CLL), it is highly desirable to reduce or even completely avoid undesired side-effects in the treatment of patients in need thereof with the CD19×CD3 bispecific single chain antibody.

It is however difficult to design a CD19×CD3 antibody-based therapy, which does not cause CNS (neurological and/or psychiatric) reactions or, to put it differently, it is desired to provide a CD19×CD13 antibody-based medical therapies with increased patient tolerability, i.e., reduced or even no undesired adverse effects such as CNS reactions.

Though pharmaceutical means and methods which allow a more gradual activation of T cell populations (see WO 2007/068354) already helped to avoid significant adverse side effects in patients treated with the CD19×CD3 bispecific single chain antibody, neurological reactions could unfortunately not be prevented by these measures, in particular in cases in which doses of more than 5 to 10 microgram per square meter per day (i.e. 24 h) of the antibody have been administered.

Thus, the technical problem underlying the present invention was to provide means and methods to overcome the above problems.

The present invention addresses this need and thus provides embodiments concerning means and methods for use in the amelioration, treatment or prophylaxis of neurological adverse effects caused by a CD3 binding domain, such as a CD19×CD3 bispecific antibody.

These embodiments are characterized and described herein and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In view of the adverse events described in the sections above, particularly the adverse CNS effects including neurological reactions observed with CD3 specific binding domains, the finding that these adverse effects can be mitigated or even prevented if the administration of the CD3-specific binding domain is accompanied or preceded by the administration of a glucocorticoid, is definitely remarkable.

Specifically, the present inventors observed that those patients, to whom a CD19×CD3 bispecific antibody was administered, encountered neurological side effects, and, further, that these neurological side effects could be prevented or alleviated by means of a glucocorticoid (pre) and/or (co)therapy.

Accordingly, the present invention establishes for the first time that glucocorticoids such as dexamethasone mitigate or even prevent neurological/psychiatric adverse effects which might occur in the course of a treatment with CD3 specific binding domains (see also the Example section).

Glucocorticoids (GCs) are still the most widely used immunosuppressive agents for the treatment of inflammatory disorders and autoimmune diseases. Glucocorticoids (GC) are a class of steroid hormones that bind to the glucocorticoid receptor (GR), which is present in almost every vertebrate animal cell, including humans. These compounds are potent anti-inflammatory agents, regardless of the inflammation's cause. Glucocorticoids suppress, inter alia, the cell-mediated immunity by inhibiting genes that code for the cytokines, IL-2, IL-3, IL-4, IL-5, IL-6, IL-8 and IFN-γ.

Cortisone which belongs to the group of GCs is an important therapeutic drug which is used to fight many ailments ranging from Addison's disease to rheumatoid arthritis. Ever since the discovery of its anti-rheumatic properties, which led to its acclaim as a wonder drug, many derivatives of cortisone with enhanced properties to better fight a specific ailment have been produced. Cortisone belongs to a group of steroids known as corticosteroids. These steroids are produced by the adrenal cortex, which is the outer part of the adrenal glands, near the kidneys. The corticosteroids are divided into two main groups: the glucocorticoids (GCs), which control fat, protein, calcium and carbohydrate metabolism, and the mineralocorticoids controlling sodium and potassium levels. Cortisone belongs to the former group, i.e. to the GCs. Cortisone and its many derivatives are used for a variety of diseases. Cortisone also helped to make organ transplants a reality due to its ability to minimize the defence reaction of the body towards foreign proteins present in the implanted organ and thus damage the functionality of the implanted organ. However, despite clinical use during more than 50 years, the specific anti-inflammatory effects of GC on different cellular compartments of the immune system are not yet clear. GCs affect nearly every cell of the immune system, and there is growing evidence for cell type-specific mechanisms.

In a first embodiment, the present invention relates to a glucocorticoid (GC) for use in the amelioration, treatment or prophylaxis of neurological adverse effects caused by a CD3 binding domain. As outlined above, these unwanted adverse effects frequently accompany a therapy with a CD3 binding domain. The present invention remedies these disadvantages and provides glucocorticoid(s) for use in the amelioration, treatment or prophylaxis of neurological adverse effects in a patient wherein said patient is subject to therapy with a CD3 binding domain. Accordingly, the present invention relates to a glucocorticoid (GC) for use in a method in the amelioration, treatment or prophylaxis of neurological adverse effects caused by a CD3 binding domain.

The present invention thus relates to a GC for use in the amelioration, treatment or prophylaxis of neurological adverse effects caused by a CD3 binding domain in a human patient, wherein said GC is to be administered prior to, concurrently with and/or subsequently to the administration of said binding domain.

Also, the present invention relates to a method of amelioration, treatment or prophylaxis of neurological adverse effects caused by a CD3 binding domain, said method comprising administering to a patient in need thereof a glucocorticoid (GC). The GC is preferably administered in an amount which is sufficient to ameliorate, treat or prevent said neurological adverse effects caused by a CD3 binding domain.

The neurological side effects are "caused by" the administration of a CD3 binding domain to a patient. The term "caused by" means that the CD3 binding domain is causative for the neurological side effects. The skilled person can easily evaluate whether the administration a CD3 binding domain is causative for a neurological effect or not. To this end, it is just required to closely monitor the patient during the course of the administration and to detect, thereby, that the administration of the CD3 binding domain was causative for the neurological side effects. Likewise, it is envisaged to discontinue the administration of the CD3 binding domain and to evaluate whether the neurological side effects are thereby ameliorated or even fade away, which also indicates that the neurological side effects were caused by said CD3 binding domain.

The term "glucocorticoid" means compounds that bind, preferably specifically, to the glucocorticoid receptor. Said term includes compound(s) selected from the group consisting of cortisone, cortisol (hydrocortisone), cloprednol, prednisone, prednisolone, methylprednisolone, deflazacort, fluocortolone, triamcinolone, (including triamcinolonacetonide), dexamethasone, betamethasone, cortivazol, paramethasone, flusticasonepropionate, triamcinolonacetonide. and/or fluticasone (including flusticasonepropionate), including pharmaceutically acceptable derivatives thereof. In the context of the embodiments of the present invention, the mentioned compounds may be used alone or in combination. Dexamethasone is preferred. The present invention is however not limited to the above mentioned specific GCs. It is envisaged that all substances which already are or will be classified as a "glucocorticoid", may be employed in the context of the present invention as well. Such future glucocorticoids include compounds which specifically bind to and activate the glucocorticoid receptor. The term "specifically binds to the GC receptor" means in accordance with the present invention that the GC (or a compound which is assumed to act like a GC) associates with (e.g., interacts with) the GC receptor (also known as NR3C1) to a statistically significant degree as compared to association with proteins/receptors generally (i.e., non-specific binding). When the GC receptor binds to glucocorticoids, its primary mechanism of action is the regulation of gene transcription. In the absence of GC, the glucocorticoid receptor (GR) resides in the cytosol complexed with a variety of proteins including Heat shock protein 90 (hsp90), the heat shock protein 70 (hsp70) and the protein FKBP52 (FK506-binding protein 52). The binding of the GC to the glucocorticoid receptor (GR) results in release of the heat shock proteins. It is thus envisaged that a future GC, or a pharmaceutically acceptable derivative or salt of a GC is preferably able to bind to the GC receptor and to release the above mentioned heat shock proteins. The activated GR complex up-regulates the expression of anti-inflammatory proteins in the nucleus or represses the expression of pro-inflammatory proteins in the cytosol (by preventing the translocation of other transcription factors from the cytosol into the nucleus).

In a preferred embodiment, said GC is selected from the most clinical used and relevant GCs like dexamethasone, fluticasonepropionate, prednisolone, methylprednisolone, betamethasone, triamcinolonacetonide or combinations thereof.

In an even more preferred embodiment, said GC is dexamethasone.

Dexamethasone has the highest glucocorticoid potency of the most commonly used steroids and also has the longest half-life (see Table below). But a person skilled in the field can select one of the other known glucocorticoids, some of which are disclosed herein, and select an appropriate effective dose to ameliorate or prevent neurological adverse events that may result from the treatment of a patient in need thereof, such as a DLBCL patient with a bispecific antibody molecule that contains a CD3 binding domain, such as CD19×CD3 bispecific single chain antibody.

| Agent | Approx. equiv. dose (mg) | Relative anti-inflammatory (glucocorticoid) potency | Relative mineralo-corticoid ($Na^+$ retaining) potency | Biologic half-life (hrs) |
| --- | --- | --- | --- | --- |
| Cortisone | 25 | 0.8 | 0.8 | 8-12 |
| Hydrocortisone | 20 | 1 | 1 | 8-12 |
| Prednisone | 5 | 4 | 0.8 | 18-36 |
| Prednisolone | 5 | 4 | 0.8 | 18-36 |
| Methylprednisolone | 5 | 5 | 0.5 | 18-36 |
| Dexamethasone | 0.75 | 25 | 0 | 36-54 |

Dexamethasone also possesses a beneficial effect in malignant central nervous system (CNS) disease (e.g. CNS lymphoma or brain metastases)—possibly due to specific penetration to the CNS. It is also preferentially (over other steroids) used to treat brain edema. Although corticosteroids decrease capillary permeability in the tumor itself, it has been found in animal models that dexamethasone may act differently and decrease edema by effects on bulk flow away from the tumor (Molnar, Lapin, & Goothuis, 1995, Neurooncol. 1995; 25(1):19-28.

For the clinical trials in connection with the application of a CD19×CD3 bispecific single chain antibody for the treatment of tumorous mass of lymph node tissue and/or extranodal lymphoma caused by DLBCL, the present inventors had to develop a treatment regime which was efficient and would be well tolerated by most of the patients. To this end, the present inventors applied a step-wise application of a CD19×CD3 bispecific single chain antibody in that 5/15/60 $\mu g/m^2/24$ h was administered to patients. Thereby, adverse effects, in particular neurological/psychiatric events could be reduced in number, ameliorated and even prevented. Also contemplated in the step-wise administration of a CD19× CD3 bispecific single chain antibody is a treatment regime using two of the dosages, such as 5/15 $\mu g/m^2/24$ h, 5/60 $\mu g/m^2/24$ h, or 15/60 $\mu g/m^2/24$ h for the duration of the patient's treatment. The appropriate dosage can be selected by the clinician on the basis of efficacy, tolerability and safety with a minimum of adverse effects in the patient.

But the inventors also contemplate the treatment of tumorous mass of lymph node tissue and/or extranodal lymphoma caused by DLBCL to include the continuous administration of a flat dose without escalation to a subsequent higher dose. For example, the present treatment regime includes the administration of 5 $\mu g/m^2/24$ h, 15 $\mu g/m^2/24$ h, or 60 $\mu g/m^2/24$ h of a CD19×CD3 bispecific single chain antibody until the conclusion of a course of the treatment up to 8 weeks [56 days] with good tolerability and no adverse effects, and even longer if determined to be safe and effective.

It is generally preferred that each of the doses disclosed herein can be converted from amount (in $\mu g$)/$m^2$/d into $\mu g$/d by multiplying the respective dose with the factor 1.9. Accordingly, each of the doses disclosed herein can be applied in the methods and uses by multiplying it with the factor 1.9. For example, a dose of 5 $\mu g/m^2/d$ is converted into 9.5 $\mu g/d$, a dose of 15 $\mu g/m^2$ is converted into 28.5 $\mu g/m^2/$ and a dose of 60 $\mu g/m^2/$ is converted into 114 $\mu g/m^2$. It is preferred that a decimal digit that results from the multiplication is either rounded up or rounded down, respectively, to a whole number. For example, a dose of 9.5 µg/d can be rounded down to 9 µg/d and a dose of 28.5 µg/m² can be rounded down to 28 µg/d. Likewise, a dose of 9.5 µg/d can be rounded up to 10 µg/d and a dose of 28.5 µg/m² can be rounded up to 29 µg/d.

The term "pharmaceutically acceptable derivatives" includes salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatisation.

The dose of the GC that is to be used in accordance with the embodiments of the present invention is not limited, i.e. it will depend on the circumstances of the individual patient. GC can be administered intravenously or orally. Preferred dosages of the GC include, however, between 1 to 6 mg (dexamethasone equivalent) at the lower end of dosing to 40 mg/d (dexamethasone equivalent). Said dosage can be administered all at once or subdivided into smaller dosages (see the appended examples). Particularly preferred is a dosage of 4 to 24 mg/d. Daily dosages of 4, 8, 12, 16, 20 or 24 mg/d are even more preferred. A dosage of 1×4 mg per day, 2×4 mg per day, 1×8 mg per day; 1×4 mg plus 1×8 mg per day, 2×8 mg per day, 2×10 mg per day or 5×4 mg per day and 3×8 mg per day of dexamethasone is particularly preferred. "d" denotes one day. Further dosage regimens are derivable from the appended examples. All dosages given in this paragraph refer to dexamethasone equivalents.

An "adverse effect", which is sometimes also denoted as "side effect" or "adverse event (in clinical studies)" is a harmful and undesired effect resulting from medication in the treatment of a patient with a CD3 binding domain. A "neurological/psychiatric adverse effect" which is sometimes also denoted as neurological symptom or CNS adverse effect, includes conditions of a human patient such as all forms of pain, including headache and back pain, muscle weakness or incoordination, abnormal sensations in the skin, and disturbances of the senses, seizures, encephalopathy, cerebral edema, confusion, ataxia, speech disorder, hallucinations, apraxia, paresis, tremor, headache, or disorientation. A neurological effect as used herein preferably includes psychiatric adverse effects. Sometimes, however, the terms "neurological adverse effect" and "psychiatric adverse effects" can be used interchangeable.

Specifically, neurological/psychiatric reactions observed during treatment with a CD3 binding domain include for example confusion and disorientation. "Confusion" as used herein refers to loss of orientation which is the ability to place oneself correctly in the world by time, location, and personal identity, and often memory which is the ability to correctly recall previous events or learn new material. The patients usually have difficulties to concentrate and thinking is not only blurred and unclear but often significantly slowed down. Patients with neurological/psychiatric reactions also suffer from loss of memory. Frequently, the confusion leads to the loss of ability to recognize people and/or places, or to tell time and the date. Feelings of disorientation are common in confusion, and the decision-making ability is impaired. Neurological reactions further comprise blurred speech and/or word finding difficulties. This disorder may impair both, the expression and understanding of language as well as reading and writing. Besides urinary incontinence, also vertigo and dizziness may accompany neurological reactions in some patients.

The herein mentioned "patient" is a mammal, preferably a human, who will be or (already) is treated with a CD3 binding domain.

It is also envisaged that the patient is characterized by a B/T-cell ratio of less than 1:5 (see PCT/EP2010/066207).

In a preferred embodiment, the patient is suspected/assumed to comprise or already comprises malignant CD19 positive lymphocytes (in particular B cells). In the latter case, said patient has already been diagnosed to comprise such cells. These malignant CD19 positive lymphocytes (in particular B cells) are present in a patient developing and/or suffering from leukemia and/or lymphoma.

A "CD3 binding domain" characterizes in connection with the present invention a binding domain which comprises a framework region and an "antigen-binding-site" or "antigen-interaction site" which is able to specifically interact with a CD3 antigen. Said binding/interaction is also understood to define a "specific recognition". The term "specifically interact/interacting" means in accordance with this invention that the binding domain is capable of binding to at least two, preferably at least three, more preferably at least four amino acids of the CD3 antigen, preferably the CD3epsilon antigen, and more preferably the human CD3epsilon antigen. Such CD3 binding domains as well as specific CD3epsilon epitopes are well-known to the skilled person and exemplified in great detail for example in WO2008119567 or in WO2008119566, both of which are included herein by way of reference thereto.

As used herein, "CD3" denotes a molecule expressed as part of the T cell receptor and has the meaning as typically ascribed to it in the prior art. In human, it encompasses in individual or independently combined form all known CD3 subunits, for example CD3 epsilon, CD3 delta, CD3 gamma, CD3 zeta, CD3 alpha and CD3 beta. The human CD3 epsilon is indicated in GenBank Accession No. NM_000733.

A CD3 binding molecule which binds to the human CD3 epsilon is preferred. The CD3epsilon epitope disclosed in great detail in WO2008119567 or in WO2008119566 is even more preferred.

The term "framework" includes a scaffold for antigen-binding sites. For example, such a scaffold could be provided by protein A, in particular, the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain or thioredoxin (Skerra, Curr. Opin. Biotechnol. 18, 295-304 (2005); Hosse et al., Protein Sci. 15, 14-27 (2006); Nicaise et al., Protein Sci. 13, 1882-1891 (2004); Nygren and Uhlen, Curr. Opin. Struc. Biol. 7, 463-469 (1997)).

A preferred "framework" is, in the context of the present invention, the art-recognized portions of an antibody variable region that exist between the more divergent (i.e., hypervariable) complementarity determining regions (CDRs) within the variable region of an antibody. Such framework regions are typically referred to as frameworks 1 through 4 (FR1, FR2, FR3, and FR4) and provide a scaffold for the presentation of the six CDRs (three from the heavy chain and three from the light chain) in three dimensional space, to form an antigen-binding surface.

A preferred example of a CD3 binding domain in line with the present invention is an antibody. The binding domain may be a monoclonal or polyclonal antibody or derived from a monoclonal or polyclonal antibody. The term "antibody" comprises derivatives or functional fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also comprises immunoglobulins (Ig's) of different classes (i.e. IgA, IgG, IgM, IgD and IgE) and subclasses (such as IgG1, IgG2 etc.).

The definition of the term "antibody" also includes embodiments such as chimeric, single chain, de-immunized and humanized antibodies, as well as antibody fragments, like, inter alia, Fab fragments. Antibody fragments or derivatives further comprise F(ab')2, Fv, scFv fragments or single domain antibodies, single variable domain antibodies or immunoglobulin single variable domain comprising merely one variable domain, which might be VH or VL, that specifically bind to an antigen or epitope independently of other V regions or domains; see, for example, Harlow and Lane (1988) and (1999), cited above. Such immunoglobulin single variable domain encompasses not only an isolated antibody single variable domain polypeptide, but also larger polypeptides that comprise one or more monomers of an antibody single variable domain polypeptide sequence.

Bispecific antibody formats are preferred; however other multispecific antibody formats (trispecifc, tetrabodies etc.) are not excluded.

In a further preferred embodiment, the present invention relates to methods of treatment/dosage regimen which employ CD19×CD3 bispecific antibodies, comprising a first binding domain capable of binding to an epitope of human CD3 epsilon chain and a second binding domain capable of binding to human CD19. Examples for bispecific molecules according to the methods of the invention are described in great detail in WO 99/54440 and WO 2004/106381 and WO 2008/119565. All the specific CD19×CD3 bispecific antibodies disclosed therein, including their variants, fragments, equivalents etc. are particularly preferred CD19×CD3 bispecific antibodies of the present invention.

As used herein, a "CD19×CD3 bispecific antibody" (including a CD19×CD3 bispecific single chain antibody) denotes a single polypeptide chain comprising two binding domains. Such single chain antibodies are preferred in the context of the methods/dosage regimen of the present invention. Each binding domain comprises at least one variable region from an antibody heavy chain ("VH or H region"), wherein the VH region of the first binding domain specifically binds to the CD3 epsilon molecule, and the VH region of the second binding domain specifically binds to CD19. The two binding domains are optionally linked to one another by a short polypeptide spacer. A non-limiting example for a polypeptide spacer is Gly-Gly-Gly-Gly-Ser (G-G-G-G-S) and repeats thereof. Each binding domain may additionally comprise one variable region from an antibody light chain ("VL or L region"), the VH region and VL region within each of the first and second binding domains being linked to one another via a polypeptide linker, for example of the type disclosed and claimed in EP 623679 B1, but in any case long enough to allow the VH region and VL region of the first binding domain and the VH region and VL region of the second binding domain to pair with one another such that, together, they are able to specifically bind to the respective first and second binding domains. Such CD19CD3 bispecific single chain antibodies are described in great detail in WO 99/54440 and WO 2004/106381.

The human CD19 protein is indicated in GenBank Accession No. AAA69966.

Preferably, the bispecific antibody applied in the methods/dosage regimens of the present invention has the domain arrangement VL(CD19)-VH(CD19)-VH(CD3)-VL(CD3).

It is, however, also envisaged that the methods of the invention can be carried out with CD19×CD3 bispecific single chain antibodies of other domain arrangements, such as VH(CD19)-VL(CD19)-VH(CD3)-VL(CD3),
VL(CD19)-VH(CD19)-VL(CD3)-VH(CD3),
VH(CD19)-VL(CD19)-VL(CD3)-VH(CD3),
VL(CD3)-VH(CD3)-VH(CD19)-VL(CD19),
VH(CD3)-VL(CD3)-VH(CD19)-VL(CD19),
VH(CD3)-VH(CD3)-VL(CD19)-VH(CD19), or
VH(CD3)-VL(CD3)-VL(CD19)-VH(CD19).

A preferred CD19×CD3 bispecific antibody applied in the methods of the present invention comprises the (a) anti-CD3 CDRs of the heavy chain shown as CD3 CDR-H1 in SEQ ID NO: 11 (RYTMH), more preferably in SEQ ID NO: 11 (GYTFTRYTMH), CD3 CDR-H2 in SEQ ID NO: 12 (YINPSRGYTNYNQKFKD) and CD3 CDR-H3 in SEQ ID NO: 13 (YYDDHYCLDY); and/or (b) anti-CD3 CDRs of the light chain shown as CD3 CDR-L1 in SEQ ID NO: 14 (RASSSVSYMN), CD3 CDR-L2 in SEQ ID NO: 15 (DTSKVAS) and CD3 CDR-L3 in SEQ ID NO: 16 (QQWSSNPLT); and/or (c) anti-CD19 CDRs of the heavy chain shown as CD19 CDR-H1 in SEQ ID NO: 17 (SYWMN), more preferably in SEQ ID NO: 17 (GYAFSSYWMN), CD19 CDR-H2 in SEQ ID NO: 18 (QIWPGDGDTNYNGKFKG) and CD19 CDR-H3 in SEQ ID NO: 19 (RETTTVGRYYYAMDY); and/or (d) anti-CD19 CDRs of the light chain shown as CD19 CDR-L1 in SEQ ID NO: 20 (KASQSVDYDGDSYLN), CD19 CDR-L2 in SEQ ID NO: 21 (DASNLVS) and CD19 CDR-L3 in SEQ ID NO: 22 (QQSTEDPWT).

It is more preferred that the CD19×CD3 bispecific antibody applied in the methods of the present invention comprises the CD3 CDRs of the heavy and light chain. Even more preferably, the CD19×CD3 bispecific antibody applied in the methods of the present invention comprises the CD3 CDRs of the heavy and light chain as well as the CD19 CDRs of the heavy and light chain.

The CDRs referred to herein are in accordance with the Kabat numbering system. The Kabat numbering scheme is a widely adopted standard for numbering the residues in an antibody in a consistent manner (Kabat et al., Sequences of Proteins of Immunological Interest, 1991).

Alternatively, it is preferred that the CD19×CD3 bispecific antibody applied in the methods of the present invention comprises the (a) CD19 variable heavy chain shown in SEQ ID NO: 3 (nucleotide sequence is shown in SEQ ID NO: 4); and/or
(b) CD19 variable light chain shown in SEQ ID NO: 5 (nucleotide sequence is shown in SEQ ID NO: 6); and/or
(c) CD3 variable heavy chain shown in SEQ ID NO: 7 (nucleotide sequence is shown in SEQ ID NO: 8); and/or
(d) CD3 variable light chain shown in SEQ ID NO: 9 (nucleotide sequence is shown in SEQ ID NO: 10).

More preferably, the CD19×CD3 bispecific antibody applied in the methods of the present invention comprises the CD19 variable heavy and light chain and/or the CD3 variable heavy and light chain. Even more preferably, the CD19×CD3 bispecific antibody applied in the methods of the present invention comprises the CD19 variable heavy and light chain as well as the CD3 variable heavy and light chain.

In another alternative, it is also preferred that said bispecific single chain antibody comprises an amino acid sequence selected from the group consisting of
(a) an amino acid sequence as depicted in SEQ ID NO: 1;
(b) an amino acid sequence encoded by a nucleic acid sequence as shown in SEQ ID NO: 2;
(c) an amino acid sequence encoded by a nucleic acid sequence having at least 70%, 80%, 90%, 95% or 99% identity to a nucleic acid sequence of (b), wherein said amino acid sequence is capable of specifically binding to CD3 and CD19; and
(d) an amino acid sequence encoded by a nucleic acid sequence which is degenerate as a result of the genetic code to a nucleotide sequence of (b), wherein said amino acid sequence is capable of specifically binding to CD3 and CD19.

It is to be understood that the sequence identity is determined over the entire amino acid sequence. For sequence alignments, for example, the programs Gap or BestFit can be used (Needleman and Wunsch J. Mol. Biol. 48 (1970), 443-453; Smith and Waterman, Adv. Appl. Math 2 (1981), 482-489), which is contained in the GCG software package (Genetics Computer Group, 575 Science Drive, Madison, Wis., USA 53711 (1991). It is a routine method for those skilled in the art to determine and identify an amino acid sequence having e.g. 70%, 80%, 90%, 95%, 96%, 97%, 98% or 99% sequence identity to the amino acid sequences of the CD19×CD3 bispecific antibody described herein (preferably MT103). For example, according to Crick's Wobble hypothesis, the 5' base on the anti-codon is not as spatially confined as the other two bases, and could thus have non-standard base pairing. Put in other words: the third position in a codon triplet may vary so that two triplets which differ in this third position may encode the same amino acid residue. Said hypothesis is well known to the person skilled in the art (see e.g. http://en.wikipedia.org/wiki/Wobble_Hypothesis; Crick, J Mol Biol 19 (1966): 548-55). It is furthermore a routine procedure for those skilled in the art to determine cytotoxic activity of such an amino acid sequence having e.g. 70%, 80%, 90%, 95%, 96%, 97%, 98% or 99% sequence identity to the nucleotide or amino acid sequences of the CD19×CD3 bispecific single chain antibody described herein. Cytotoxic activity of the CD19×CD3 bispecific single chain antibody or an antibody construct having e.g. 70%, 80%, 90%, 95%, 96%, 97%, 98% or 99% sequence identity to the amino acid sequences of the CD19×CD3 bispecific single chain antibody can be determined by methods as illustrated e.g. in WO 99/54440.

Particularly preferred, said CD19×CD3 bispecific single chain antibody has the amino acid sequence shown in SEQ ID NO: 1.

Also particularly preferred is the CD19×CD3 bispecific antibody MT103 described in WO 99/54440 as well as those CD19×CD3 bispecific antibodies described in WO 2004/106381 and WO 2008/119565.

The present invention also relates to a CD19×CD3 bispecific antibody for use in the treatment of malignant CD19 positive lymphocytes in a human patient, wherein said antibody is to be administered prior to, concurrently with or subsequently to the administration of a GC.

The present invention further relates to a method for
(i) administering a CD3 binding domain, such as a CD19× CD3 bispecific antibody to a human patient, or
(ii) treating malignant CD19 positive lymphocytes in a human patient by administering the CD3 binding domain; wherein said antibody is to be administered prior to, subsequently to and/or in combination with a GC.

The administration of the CD3 binding domain or of a pharmaceutical composition comprising said CD3 binding domain is preferably an intravenous administration. The administration of the GC or a pharmaceutical composition comprising said GC is preferably intravenous or per os (p.o.). They may be administered as a bolus injection or continually (continuously), with continually being preferred. A continual administration refers to an administration which is essentially without interruption. "Essentially without interruption" includes a continual administration usually without an uninterrupted flow or spatial extension. By way of example, WO 2007/068354 discloses a treatment regimen which is specifically included herein by way of reference thereto. Other treatment regimens which are envisaged in the context of the present invention are disclosed in PCT/EP2010/066207.

In a preferred embodiment, a first dose of the CD3 binding domain is administered for a first period of time; and optionally consecutively a second dose of the CD3 binding domain is administered for a second period of time, wherein the second dose exceeds the first dose.

The term "exceeds" means that the second period of time is at least one day longer than the first period of time.

In another preferred embodiment of the present application, a third dose of the CD3 binding domain is administered for a third period of time after administering a first and second dose for a first and second period of time. Accordingly, the present invention provides a three-stage (three-step) administration scheme (dosage regimen) to be applied in the uses and methods described herein.

In a further preferred embodiment, the present invention encompasses the continuous administration of a flat dose of the CD3 binding domain without escalation to a subsequent higher dose. For example, the present administration includes the administration of 60 $\mu g/m^2/24$ h, 15 $\mu g/m^2/24$ h or 5 $\mu g/m^2/24$ h of a CD3 binding domain, in particular a CD19×CD3 bispecific single chain antibody until the conclusion of a course of the treatment up to 8 weeks [56 days] and even longer if determined to be safe and effective.

More specifically, in a three-stage administration scheme, dexamethasone is administered in the range of between 6 and 48 hours before the administration of the first dose of the CD3 binding domain, more preferably between 6 and 12 hours, and more preferably 12 hours, before the first dose administration. Then approximately 1 hour before (range 15 min-2 h including 30 min, 45 min, 60 min, 75 min, 90 min) the first dose of the binding domain is administered, a dose of dexamethasone is again administered to the patient. Then dexamethasone is administered 1 or more days, preferably 2 to 3 days, after the first dose of the antibody, preferably on the two days after the first binding domain administration and administered 1 or more days, preferably 2 or more days after each dose increase, preferably on the two days after the administration of the dose increase of the binding domain. Each of the dexamethasone doses is preferably between 6 and 40 mg, and preferably at approximately 20 or 24 mg per dose.

The time range between 6 and 48 hours includes the administration of the dexamethasone dose and means that the times prior to the first administration of the binding domain are 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48 hours. Similarly, the preferred time range between 6 and 12 hours includes the administration of the dexamethasone dose prior to the first administration of the binding domain and includes 6, 7, 8, 9, 10, 11 and 12 hours, In a further embodiment, dexamethasone is administered for a period of two, three, four or five days during which the dose of the binding domain is increased. For example, dexamethasone is administered at a first point of time in a dose of 6 to 40 mg or 6 to 48 mg, preferably 20, 24, 28, 32, 36, 40, 44 or 48 mg, with 20 or 24 mg being preferred, at a second point of time in a dose of preferably 8, 12, 16, 20, or 24 mg, with 16 mg being preferred and/or at a third point of time in a dose of preferably 2, 4, 6, 8, 10 or 12 mg, with 8 mg being preferred. It may also be administered at a fourth point of time or fourth and fifth point of time in a dose of preferably 2, 4, 6, 8, 10 or 12 mg, with 8 mg being preferred.

It is also envisaged that the human patient of the present invention is characterized by a B/T-cell ratio of less than 1:5 (see PCT/EP2010/066207). As disclosed in great detail in PCT/EP2010/066207, neurological side effects frequently accompany the administration of a CD19×CD3 bispecific antibody in patients which are characterized by a B/T-cell ratio of less than 1:5. The prevention, amelioration or treatment of neurological side effects caused by a CD3 binding domain by way of a GC therapy disclosed herein, is however also applicable to patients which are characterized by a B/T-cell ratio of more than 1:5 (see PCT/EP2010/066207).

The present invention also relates to a (pharmaceutical) kit or package comprising a GC and/or a CD3 binding domain, and instructions and/or an imprint indicating that the GC is to be employed for the treatment amelioration and/or prophylaxis of neurological adverse events caused by said CD3 binding domain. Said GC and CD3 binding domain are preferably packaged together in one sealed package or kit. It is also envisaged that the package or kit of the present invention, further comprises means to administer the GC and/or Cd3 binding domain to a patient and/or buffers, vials, teflon bags or infusion bags which are normally used for the infusion of therapeutic agents. "Means" thereby includes one or more article(s) selected from the group consisting of a syringe, a hypodermic needle, a cannula, a catheter, an infusion bag for intravenous administration, intravenous vehicles, vials, buffers, stabilizers, written instructions which aid the skilled person in the preparation of the respective doses and infusions of the invention etc.

By "complete response" is intended an absence of clinically detectable disease with normalization of any previously abnormal imaging studies such as radiographic studies. Such a response preferably persists for at least 4 to 8 weeks, sometimes 6 to 8 weeks or more than 8, 10, 12, 14, 16, 18 or 20 weeks or longer, following treatment according to the invention. Alternatively, an improvement in the disease may be categorized as being a partial response.

Preferably, complete remission in ALL is defined as a blast count below 5% in the bone marrow and recovery of bone marrow function. Detailed remission and response definitions for NHL patients are used according to Cheson et al., 1999, J Clin Oncol. April; 17(4): 1244

By "partial response" is intended at least about a 50% decrease in all measurable tumor burden (i.e., the number of malignant cells present in the patient, or the measured bulk of tumor masses) in the absence of new lesions and persisting for 4 to 8 weeks or more than 8, 10, 12, 14, 16, 18 or 20 weeks or longer. A "complete response" does, however, not necessarily indicate that a disease has been cured, since a patient may relapse. However, if so, the patient can again be treated with a composition comprising a CD19×CD3 bispecific antibody as described herein.

EXAMPLES

The following examples illustrate the invention. These examples should not be construed as to limit the scope of this invention. The examples are included for purposes of illustration and the present invention is limited only by the claims.

Patients have been treated with blinatumomab and the co-medication of dexamethasone worked as amelioration, treatment or prophylaxis of neurological and/or psychiatric adverse events.

The administration of therapeutic dexamethasone was beneficial in that neurological and/or psychiatric symptoms disappeared without necessity to stop treatment by Blinatumomab.

Patient 109-015 with follicular lymphoma received blinatumomab at a dose of 60 µg/m²/d right from treatment start (i.e. without dose escalation step) for 4 weeks, the patient additionally received dexamethasone on days 4-5: 3×8 mg p.o. and on days 6-7: 1×8 mg p.o. in order to treat headache. This treatment cycle had not to be discontinued due to neurological/psychiatric adverse events.

Patient 109-017 with follicular lymphoma received blinatumomab at a dose of 60 µg/m²/d right from treatment start (i.e. without dose escalation step) for 5 weeks; in order to treat tremor dexamethasone was given p.o.: day 7: 8 mg-4 mg-4 mg; day 8+9: 8 mg-4 mg-0 mg; day 10-11: 4 mg-4 mg-0 mg; day 12-15: 4 mg-0 mg-0 mg)). This treatment cycle had not to be discontinued due to neurological/psychiatric adverse events.

Patient 109-026 with MCL received blinatumomab at a dose of 5 µg/m²/d for 1 week followed by 60 µg/m²/d for the remaining 6 weeks. The patient received dexamethasone p.o. in order to treat apraxia on day d11: 3×8 mg and on day 12: 2×8 mg. This treatment cycle had not to be discontinued due to neurological/psychiatric adverse events.

Patient 135-001 with DLBCL received blinatumomab at 5 µg/m²/d for one week, at 15 µg/m²/d for the 2$^{nd}$ week, and 60 µg/m²/d for 4 more days. The patient received dexamethasone in order to treat tremor at 5 µg/m²/d on d3 (3×8 mg) continued in decreasing dose over less than a week. There were no neurological events after escalation to 15 ug, which could be explained by a prophylactic effect of dexamethasone. However, on day 4 after step to 60 ug/m²/d the patient had to stop due to neurological/psychiatric adverse events which occurred too fast to intervene with dexamethasone.

Patient 109-036 with follicular lymphoma was treated with 5 µg/m²/d for the first week followed by treatment at 60 µg/m²/d blinatumomab for the remaining 6 weeks of treatment. The patient experienced neurological adverse events (tremor and apraxia) starting on day 11, i.e. four days after the step to 60 µg/m²/d. Dexamethasone was administered i.v. (3×8 mg) and the neurological adverse events resolved under continued treatment with blinatumomab.

Patient 109-038 with DLBCL received blinatumomab at 5 µg/m²/d for one week, at 15 µg/m²/d for the 2$^{nd}$ week, and 60 µg/m²/d for the remaining 6 weeks of treatment. On day 15, the patient developed intention tremor which resolved after dexamethasone (3×8 mg i.v.) was given (continued blinatumomab treatment).

Patient 109-039 with MCL received blinatumomab at 5 µg/m²/d for one week, at 15 µg/m²/d for the 2$^{nd}$ week, and 60 µg/m²/d for the remaining 12 days of treatment. On day 17, the patient developed tremor and slight speech disturbance which resolved after dexamethasone; 3×8 mg of dexamethasone i.v. was given (continued blinatumomab treatment).

Patient 153-002 with MCL received blinatumomab at 5 µg/m²/d for one week, at 15 µg/m²/d for the 2$^{nd}$ week, and 60 µg/m²/d for one week. The patient developed slight speech problems on day 4 which completely resolved after dexamethasone was given (3×8 mg p.o.), in decreasing doses over a few days. On day 22 the patient had to stop treatment due to paresis which disappeared without intervention.

Besides the therapeutic use of dexamethasone to mitigate neurological adverse events, dexamethasone was also used as prophylaxis in order to prevent neurological adverse events.

Patient 135-002 with DLBCL received blinatumomab at 5 µg/m²/d for one week, at 15 µg/m²/d for the 2$^{nd}$ week, and 60 µg/m²/d for the remaining 2 weeks and in addition received dexamethasone prophylaxis (dose: 3×8 mg on day of start of blinatumomab treatment and on days of dose escalation steps). The patient did not have to discontinue treatment with blinatumomab due to neurological adverse events.

In patient 155-001 in trial 103-206 with relapsed ALL, was treated with a continuous infusion of blinatumomab at a dosage of 15 µg/m2/d for 16 days. The patient was administered dexamethasone before the administration of blinatumomab in accordance with the teaching of the present application Specifically, dexamethasone prophylaxis was given (8 mg before treatment start): The patient did not have to discontinue treatment due to adverse events. The patient achieved a complete remission.

Each of the following 5 patients in trial 103-104 (all with DLBCL) were treated with blinatumomab continuous infusion at 5 µg/m2/d for the 1$^{st}$ week, then 15 µg/m2/d for the 2nd$^t$ week, and then 60 µg/m2/d for the remaining treatment period that could an additional 2-6 weeks. Also each of the following patients were treated prophylactically with 20 mg of dexamethasone at twelve hours and 1 hour before the start of blinatumomab treatment and before each dose increase from the 5 to 15 µg and from 15 to 60 µg.

Patients 135-003 did not have to discontinue due to neurological/psychiatric adverse events.

Patient 108-007 did not have to discontinue due to neurological/psychiatric adverse events. This patient achieved a complete remission of the lymphoma.

Patient 108-008 did not have to discontinue due to neurological/psychiatric adverse events.

Patient 108-009 did not have to discontinue due to neurological/psychiatric adverse events. This patient achieved an objective response of the lymphoma.

Patient 108-010 additionally received 100 mg prednisolone one hour before start of infusion. The patient did not have to discontinue due to neurological/psychiatric adverse events.

Dexamethasone was used as a prophylaxis for neurological adverse events in a 14-y female patient with ALL who was treated with 15 µg/m²/d blinatumomab on a named patient compassionate use base. 4 weeks in first cycle The patient received dexamethasone on day 1: 3×6 mg p.o., on day 2: 2×6 mg p.o. and on day 3: lx 6 mg). The patient did not have to discontinue treatment due to adverse events. The patient achieved a complete remission.

A Phase I clinical trial was performed in patients with various B-NHL including DLBCL to evaluate the CD19×CD3 bispecific antibody construct in DLBCL patients. Patients were treated for 4-8-weeks by continuous i.v. administration of the antibody with the following step-wise dosing regimen: first week at 5 µg/m²/d, second week at 15 µg/m²/d and for the remaining treatment period at 60 µg/m²/d. Two cohorts each with 6 DLBCL patients were enrolled. The two cohorts solely differed by the dose and schedule of the glucocorticoid medication administered at the beginning of the antibody infusion for mitigation of adverse events.

Out of the twelve patients, 5 were male and 7 female. The median age was 57 years (range from 24 to 78 years). Patients had received a median of 4 prior regimens (range from 2-6). All patients had been exposed to rituximab. Eight of the 12 patients had undergone ASCT. International prognostic index (IPI) at screening ranged from 1 to 3 with a median of 2. In the first cohort 100 mg prednisolone was administered 1 hour prior to start; and in the second cohort patients received dexamethasone (3×8 mg) on days 1, 2, and 3. Before treatment start in the second cohort 20 mg dexamethasone was administered at 12 hours and 1 hour prior to the administration of a CD19×CD3 bispecific antibody construct Although just one DLT (reversible CNS event grade 3) occurred in the prednisolone DLBCL cohort and, thus, the cohort is considered safe, a further DLBCL cohort applying prophylactic dexamethasone (3×8 mg at start of infusion or dose increase and reduction to 3×6 mg or 3×4 mg on the following 2 days, respectively) was opened to optimize management of CNS events. In light of one of the first two patients having a DLT due to a reversible CNS adverse event, a modified "early dexamethasone" schedule (20 mg at −12 to −6 hours and −1 hour, at start of infusion or dose increase, and 3×8 mg during the following 2 days) was introduced to test if earlier and more intensive administration of dexamethasone may ameliorate CNS adverse events. No further DLTs were observed after this adjustment of the dexamethasone schedule. Thus, both the dexamethasone cohort as well as the "early dexamethasone administration" are considered safe. Among a total of 5 patients with DLBCL treated with the "early dexamethasone schedule" no DLT was observed. Therefore, it was concluded that additional administration of "early dexamethasone" is the safest way to administer blinatumomab to patients with DLBCL. Also for patients with "early dexamethasone" objective responses have been observed.

The invention claimed is:

1. A method for preventing, ameliorating, or treating an adverse neurological event in a subject,
wherein the adverse neurological event is confusion, loss of memory, ataxia, speech disorder, disorientation, seizures, encephalopathy, cerebral edema, hallucinations, apraxia, paresis, or tremor caused by administering to the subject an antibody or fragment thereof comprising a CD3 binding domain comprising an anti-CD3 heavy chain comprising a CDR-H1 comprising the amino acid sequence of SEQ ID NO: 11, a CDR-H2 comprising the amino acid sequence of SEQ ID NO: 12, and a CDR-H3 comprising the amino acid sequence of SEQ ID NO: 13, and an anti-CD3 light chain comprising a CDR-L1 comprising the amino acid sequence of SEQ ID NO: 14, a CDR-L2 comprising the amino acid sequence of SEQ ID NO: 15, and a CDR-L3 comprising the amino acid sequence of SEQ ID NO: 16,
the method comprising the step of administering an effective amount of a glucocorticoid (GC) to the subject prior to or concurrently with administering a first dose of the antibody or fragment thereof comprising the CD3 binding domain, and prior to the presence of the adverse neurological event in the subject.

2. The method of claim 1 wherein the GC is dexamethasone.

3. The method of claim 1, wherein the GC is administered prior to the CD3 binding domain.

4. The method of claim 1, wherein a first dose of the CD3 binding domain is administered for a first period of time and consecutively a second dose of the CD3 binding domain is administered for a second period of time, wherein the second dose exceeds the first dose.

5. The method of claim 4, wherein after a first and second dose of the CD3 binding domain for a first and second period of time, the method further comprises administering a third dose of the CD3 binding domain, wherein the third dose exceeds the first and second dose.

6. The method of claim 4, wherein the GC is administered prior to the administration of the first dose of the CD3 binding domain and prior to the administration of the second dose and/or third dose of the CD3 binding domain.

7. The method of claim 1, wherein the GC is administered concurrently with the CD3 binding domain.

8. The method of claim 1, wherein said CD3 binding domain is a bispecific single chain antibody.

9. The method of claim 8, wherein the bispecific single chain antibody is a CD19×CD3 bispecific single chain antibody.

10. The method of claim 9, wherein the CD19×CD3 bispecific single chain antibody is MT103.

11. The method of claim 1, wherein the patient is a human.

12. The method of claim 1, wherein the patient is characterized by a B/T-cell ratio of less than 1:5.

13. The method of claim 1, wherein the CD3 binding domain is a CD3 epsilon binding domain.

14. The method of claim 1, wherein the antibody comprises
   an anti-CD3 heavy chain comprising a CDR-H1 comprising the amino acid sequence of SEQ ID NO: 11, a CDR-H2 comprising the amino acid sequence of SEQ ID NO: 12, and a CDR-H3 comprising the amino acid sequence of SEQ ID NO: 13;
   an anti-CD3 light chain comprising a CDR-L1 comprising the amino acid sequence of SEQ ID NO: 14, a CDR-L2 comprising the amino acid sequence of SEQ ID NO: 15, and a CDR-L3 comprising the amino acid sequence of SEQ ID NO: 16;
   an anti-CD19 heavy chain comprising a CDR-H1 comprising the amino acid sequence of SEQ ID NO: 17, a CDR-H2 comprising the amino acid sequence of SEQ ID NO: 18, and a CDR-H3 comprising the amino acid sequence of SEQ ID NO: 19; and
   an anti-CD19 light chain comprising a CDR-L1 comprising the amino acid sequence of SEQ ID NO: 20, a CDR-L2 comprising the amino acid sequence of SEQ ID NO: 21, and a CDR-L3 comprising the amino acid sequence of SEQ ID NO: 22.

15. The method of claim 1, wherein the antibody comprises
   an anti-CD3 heavy chain comprising the amino acid sequence of SEQ ID NO: 7 or comprising an amino acid sequence encoded by the nucleotide sequence of SEQ ID NO: 8;
   an anti-CD3 light chain comprising the amino acid sequence of SEQ ID NO: 9 or comprising an amino acid sequence encoded by the nucleotide sequence of SEQ ID NO: 10;
   an anti-CD19 heavy chain comprising the amino acid sequence of SEQ ID NO: 3 or comprising an amino acid sequence encoded by the nucleotide sequence of SEQ ID NO: 4; and
   an anti-CD19 light chain comprising the amino acid sequence of SEQ ID NO: 5 or comprising an amino acid sequence encoded by the nucleotide sequence of SEQ ID NO: 6.

16. The method of claim 1, wherein the antibody comprises an amino acid sequence selected from the group consisting of:
   (a) the amino acid sequence set forth in SEQ ID NO: 1;
   (b) an amino acid sequence encoded by the nucleotide sequence set forth in SEQ ID NO: 2; and
   (c) an amino acid sequence encoded by a nucleotide sequence having at least 70% identity to the nucleotide sequence set forth in SEQ ID NO: 2.

* * * * *

SEQUENCE LISTING

```
<160> NUMBER OF SEQ ID NOS: 22

<210> SEQ ID NO 1
<211> LENGTH: 498
<212> TYPE: PRT
<213> ORGANISM: Artificial Sequence
<220> FEATURE:
<223> OTHER INFORMATION: CD19xCD3 bispecific single chain antibody
```

-continued

<400> SEQUENCE: 1

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
            325                 330                 335

Gln Leu Ser Ser Leu Thr Ser Glu Asp Ser Ala Val Tyr Tyr Cys Ala
        340                 345                 350

Arg Tyr Tyr Asp Asp His Tyr Cys Leu Asp Tyr Trp Gly Gln Gly Thr
    355                 360                 365

Thr Leu Thr Val Ser Ser Val Glu Gly Gly Ser Gly Gly Ser Gly Gly
370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
```

```
                    405                 410                 415
Ala Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
                435                 440                 445

Val Pro Tyr Arg Phe Ser Gly Ser Gly Ser Gly Thr Ser Tyr Ser Leu
        450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys

<210> SEQ ID NO 2
<211> LENGTH: 1494
<212> TYPE: DNA
<213> ORGANISM: Artificial Sequence
<220> FEATURE:
<223> OTHER INFORMATION: CD19xCD3 bispecific single chain antibody

<400> SEQUENCE: 2
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac caggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaaggtggtg gtggttctgg cggcggcggc     360
tccggtggtg gtggttctca ggtgcagctg cagcagtctg ggctgagct ggtgaggcct     420
gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca cagcctacat gcaactcagc agcctagcat ctgaggactc tgcggtctat     660
ttctgtgcaa gacgggagac tacgacggta ggccgttatt actatgctat ggactactgg     720
ggccaaggga ccacggtcac cgtctcctcc ggaggtggtg gatccgatat caaactgcag     780
cagtcagggg ctgaactggc aagacctggg gcctcagtga agatgtcctg caagacttct     840
ggctacacct ttactaggta cacgatgcac tgggtaaaac agaggcctgg acagggtctg     900
gaatggattg gatacattaa tcctagccgt ggttatacta attacaatca gaagttcaag     960
gacaaggcca cattgactac agacaaatcc tccagcacag cctacatgca actgagcagc    1020
ctgacatctg aggactctgc agtctattac tgtgcaagat attatgatga tcattactgc    1080
cttgactact ggggccaagg caccactctc acagtctcct cagtcgaagg tggaagtgga    1140
ggttctggtg gaagtggagg ttcaggtgga gtcgacgaca ttcagctgac ccagtctcca    1200
gcaatcatgt ctgcatctcc aggggagaag gtcaccatga cctgcagagc cagttcaagt    1260
gtaagttaca tgaactggta ccagcagaag tcaggcacct cccccaaaag atggatttat    1320
gacacatcca agtggcttc tggagtccct tatcgcttca gtggcagtgg gtctgggacc    1380
tcatactctc tcacaatcag cagcatggag gctgaagatg ctgccactta ttactgccaa    1440
cagtggagta gtaacccgct cacgttcggt gctgggacca agctggagct gaaa          1494
```

<210> SEQ ID NO 3
<211> LENGTH: 124
<212> TYPE: PRT
<213> ORGANISM: Artificial Sequence
<220> FEATURE:
<223> OTHER INFORMATION: VH anti CD19

<400> SEQUENCE: 3

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 4
<211> LENGTH: 372
<212> TYPE: DNA
<213> ORGANISM: Artificial Sequence
<220> FEATURE:
<223> OTHER INFORMATION: VH anti CD19

<400> SEQUENCE: 4

```
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg gagatggtga tactaactac     180
aatggaaagt tcaagggtaa agccactctg actgcagacg aatcctccag cacagcctac     240
atgcaactca gcagcctagc atctgaggac tctgcggtct atttctgtgc aagacgggag     300
actacgacgg taggccgtta ttactatgct atggactact ggggccaagg gaccacggtc     360
accgtctcct cc                                                         372
```

<210> SEQ ID NO 5
<211> LENGTH: 111
<212> TYPE: PRT
<213> ORGANISM: Artificial Sequence
<220> FEATURE:
<223> OTHER INFORMATION: VL anti CD19

<400> SEQUENCE: 5

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60
```

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 6
<211> LENGTH: 333
<212> TYPE: DNA
<213> ORGANISM: Artificial Sequence
<220> FEATURE:
<223> OTHER INFORMATION: VL anti CD19

<400> SEQUENCE: 6
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaa                                   333

<210> SEQ ID NO 7
<211> LENGTH: 119
<212> TYPE: PRT
<213> ORGANISM: Artificial Sequence
<220> FEATURE:
<223> OTHER INFORMATION: VH anti CD3

<400> SEQUENCE: 7

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 8
<211> LENGTH: 357
<212> TYPE: DNA
<213> ORGANISM: Artificial Sequence
<220> FEATURE:
<223> OTHER INFORMATION: VH anti CD3

<400> SEQUENCE: 8
gatatcaaac tgcagcagtc aggggctgaa ctggcaagac ctggggcctc agtgaagatg      60
tcctgcaaga cttctggcta cacctttact aggtacacga tgcactgggt aaaacagagg     120

```
cctggacagg gtctggaatg gattggatac attaatccta gccgtggtta tactaattac    180
aatcagaagt tcaaggacaa ggccacattg actacagaca atcctccag cacagcctac     240 atgcaactga gcagcctgac atctgaggac tctgcagtct attactgtgc aagatattat    300
gatgatcatt actgccttga ctactggggc caaggcacca ctctcacagt ctcctca       357
```

<210> SEQ ID NO 9
<211> LENGTH: 106
<212> TYPE: PRT
<213> ORGANISM: Artificial Sequence
<220> FEATURE:
<223> OTHER INFORMATION: VL anti CD3

<400> SEQUENCE: 9

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105
```

<210> SEQ ID NO 10
<211> LENGTH: 318
<212> TYPE: DNA
<213> ORGANISM: Artificial Sequence
<220> FEATURE:
<223> OTHER INFORMATION: VL anti CD3

<400> SEQUENCE: 10

```
gacattcagc tgacccagtc tccagcaatc atgtctgcat ctccagggga gaaggtcacc    60
atgacctgca gagccagttc aagtgtaagt tacatgaact ggtaccagca gaagtcaggc    120
acctccccca aaagatggat ttatgacaca tccaaagtgg cttctggagt cccttatcgc    180
ttcagtggca gtgggtctgg gacctcatac tctctcacaa tcagcagcat ggaggctgaa    240
gatgctgcca cttattactg ccaacagtgg agtagtaacc cgctcacgtt cggtgctggg    300
accaagctgg agctgaaa                                                  318
```

<210> SEQ ID NO 11
<211> LENGTH: 10
<212> TYPE: PRT
<213> ORGANISM: artificial
<220> FEATURE:
<223> OTHER INFORMATION: CD3 CDR-H1

<400> SEQUENCE: 11

```
Gly Tyr Thr Phe Thr Arg Tyr Thr Met His
1               5                   10
```

<210> SEQ ID NO 12
<211> LENGTH: 17
<212> TYPE: PRT

-continued

```
<213> ORGANISM: artificial
<220> FEATURE:
<223> OTHER INFORMATION: CD3 CDR-H2

<400> SEQUENCE: 12

Tyr Ile Asn Pro Ser Arg Gly Tyr Thr Asn Tyr Asn Gln Lys Phe Lys
1               5                   10                  15

Asp

<210> SEQ ID NO 13
<211> LENGTH: 10
<212> TYPE: PRT
<213> ORGANISM: artificial
<220> FEATURE:
<223> OTHER INFORMATION: CD3 CDR-H3

<400> SEQUENCE: 13

Tyr Tyr Asp Asp His Tyr Cys Leu Asp Tyr
1               5                   10

<210> SEQ ID NO 14
<211> LENGTH: 10
<212> TYPE: PRT
<213> ORGANISM: artificial
<220> FEATURE:
<223> OTHER INFORMATION: CD3 CDR-L1

<400> SEQUENCE: 14

Arg Ala Ser Ser Ser Val Ser Tyr Met Asn
1               5                   10

<210> SEQ ID NO 15
<211> LENGTH: 7
<212> TYPE: PRT
<213> ORGANISM: artificial
<220> FEATURE:
<223> OTHER INFORMATION: CD3 CDR-L2

<400> SEQUENCE: 15

Asp Thr Ser Lys Val Ala Ser
1               5

<210> SEQ ID NO 16
<211> LENGTH: 9
<212> TYPE: PRT
<213> ORGANISM: artificial
<220> FEATURE:
<223> OTHER INFORMATION: CD3 CDR-L3

<400> SEQUENCE: 16

Gln Gln Trp Ser Ser Asn Pro Leu Thr
1               5

<210> SEQ ID NO 17
<211> LENGTH: 10
<212> TYPE: PRT
<213> ORGANISM: artificial
<220> FEATURE:
<223> OTHER INFORMATION: CD19 CDR-H1

<400> SEQUENCE: 17

Gly Tyr Ala Phe Ser Ser Tyr Trp Met Asn
1               5                   10

<210> SEQ ID NO 18
<211> LENGTH: 17
```

```
<212> TYPE: PRT
<213> ORGANISM: artificial
<220> FEATURE:
<223> OTHER INFORMATION: CD19 CDR-H2

<400> SEQUENCE: 18

Gln Ile Trp Pro Gly Asp Gly Asp Thr Asn Tyr Asn Gly Lys Phe Lys
1               5                   10                  15

Gly

<210> SEQ ID NO 19
<211> LENGTH: 15
<212> TYPE: PRT
<213> ORGANISM: artificial
<220> FEATURE:
<223> OTHER INFORMATION: CD19 CDR-H3

<400> SEQUENCE: 19

Arg Glu Thr Thr Thr Val Gly Arg Tyr Tyr Tyr Ala Met Asp Tyr
1               5                   10                  15

<210> SEQ ID NO 20
<211> LENGTH: 15
<212> TYPE: PRT
<213> ORGANISM: artificial
<220> FEATURE:
<223> OTHER INFORMATION: CD19 CDR-L1

<400> SEQUENCE: 20

Lys Ala Ser Gln Ser Val Asp Tyr Asp Gly Asp Ser Tyr Leu Asn
1               5                   10                  15

<210> SEQ ID NO 21
<211> LENGTH: 7
<212> TYPE: PRT
<213> ORGANISM: artificial
<220> FEATURE:
<223> OTHER INFORMATION: CD19 CDR-L2

<400> SEQUENCE: 21

Asp Ala Ser Asn Leu Val Ser
1               5

<210> SEQ ID NO 22
<211> LENGTH: 9
<212> TYPE: PRT
<213> ORGANISM: artificial
<220> FEATURE:
<223> OTHER INFORMATION: CD19 CDR-L3

<400> SEQUENCE: 22

Gln Gln Ser Thr Glu Asp Pro Trp Thr
1               5
```